United States Patent
Jung et al.

(10) Patent No.: US 9,304,135 B2
(45) Date of Patent: Apr. 5, 2016

(54) METHOD FOR DIAGNOSING STOMACH CANCER USING CHANGE OF TRYPTOPHAN METABOLISM

(71) Applicant: KOREA INSTITUTE OF SCIENCE AND TECHNOLOGY, Seoul (KR)

(72) Inventors: Byung Hwa Jung, Seoul (KR); Soo Hyun Lee, Seoul (KR); Myung Soo Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/315,455

(22) Filed: Jun. 26, 2014

(65) Prior Publication Data
US 2015/0053852 A1 Feb. 26, 2015

(30) Foreign Application Priority Data
Jun. 26, 2013 (KR) ........................ 10-2013-0073536

(51) Int. Cl.
*G01N 33/49* (2006.01)
*G01N 30/72* (2006.01)
*H01J 49/00* (2006.01)
*G01N 33/574* (2006.01)
*G01N 33/68* (2006.01)

(52) U.S. Cl.
CPC ........ *G01N 33/57446* (2013.01); *G01N 33/492* (2013.01); *G01N 30/7233* (2013.01); *G01N 33/6812* (2013.01); *G01N 33/6848* (2013.01); *G01N 2800/06* (2013.01); *G01N 2800/60* (2013.01); *H01J 49/00* (2013.01); *Y10T 436/24* (2015.01)

(58) Field of Classification Search
CPC ..... G01N 33/48; G01N 33/49; G01N 33/492; G01N 33/50; G01N 33/68; G01N 33/6806; G01N 33/6812; G01N 33/6848; G01N 33/6851; G01N 33/6893; G01N 30/72; G01N 30/7233; G01N 2800/06; H01J 49/00; Y10T 436/145555; Y10T 436/17; Y10T 436/173845; Y10T 436/18; Y10T 436/20; Y10T 436/200833; Y10T 436/201666; Y10T 436/203332; Y10T 436/24; Y10T 436/25; Y10T 436/25125

USPC ......... 436/63, 64, 86, 89, 106, 111, 127, 128, 436/129, 131, 96, 119, 161, 173, 174, 175; 422/70; 435/29; 250/281, 282
See application file for complete search history.

(56) References Cited

U.S. PATENT DOCUMENTS

| | | | |
|---|---|---|---|
| 5,879,880 A | 3/1999 | Koca et al. | |
| 6,405,070 B1 * | 6/2002 | Banerjee | A61B 5/0071 436/64 |
| 2009/0047269 A1 * | 2/2009 | Chinnaiyan | C12N 5/0693 424/94.5 |
| 2011/0151497 A1 * | 6/2011 | Chinnaiyan | G01N 33/57415 435/29 |

FOREIGN PATENT DOCUMENTS

| | | |
|---|---|---|
| JP | 2010-537170 A | 12/2010 |
| JP | 2013-515270 A | 5/2013 |
| KR | 10-2011-0079870 | 7/2011 |
| WO | WO2009-026152 A1 | 2/2009 |
| WO | WO 2009/110517 A1 | 9/2009 |
| WO | WO2011-087845 A2 | 7/2011 |

OTHER PUBLICATIONS

Engin et al. Abstract from Pteridines, vol. 21 (4), 2010, pp. 110-120.*
Schroecksnadel et al. Journal of Cancer Research and Clinical Oncology, vol. 133, 2007, pp. 477-485.*
Robert Sucher et al., "IDO-Mediated Tryptophan Degradation in the Pathogenesis of Malignant Tumor Disease", *International Journal of Tryptophan Research*, 2010, pp. 113-120.
Devita Surjana et al., "Role of Nicotinamide in DNA Damage, Mutagenesis, and DNA Repair", *Journal of Nucleic Acids*, 2010, pp. 1-13, vol. 2010.
Wentao Zhu et al., "Quantitative profiling of tryptophan metabolites in serum, urine, and cell culture supernatants by liquid chromatography-tandem mass spectrometry", *Anal Bioanal Chem*, 2011, pp. 3249-3261, vol. 401, No. 10.

* cited by examiner

*Primary Examiner* — Maureen Wallenhorst
(74) *Attorney, Agent, or Firm* — Goldilocks Zone IP Law

(57) ABSTRACT

The present disclosure relates to stomach cancer diagnosis using tryptophan metabolism rate in one aspect, and it relates to an invention using change of tryptophan metabolism rate in a stomach cancer patient, which is different from a normal person.

4 Claims, 4 Drawing Sheets

METHOD FOR DIAGNOSING STOMACH CANCER USING CHANGE OF TRYPTOPHAN METABOLISM

CROSS-REFERENCE TO RELATED APPLICATION

This application claims priority to Korean Patent Application No. 10-2013-0073536, filed on Jun. 26, 2013, and all the benefits accruing therefrom under 35 U.S.C. §119, the contents of which in its entirety are herein incorporated by reference.

BACKGROUND

1. Field

The present disclosure relates to a method for providing information, which helps judge whether cancer occurs or not by using tryptophan metabolism rate in one aspect.

[Description about National Research and Development Support]

This study was supported by Korea Institute of Science and Technology and Korea Research Council of Fundamental Science and Technology of Ministry of Science, ICT and Future Planning, Republic of Korea (Project Nos. 1711008930, 1345194445) under Korea Institute of Science and Technology.

2. Description of the Related Art

Tryptophan is an essential amino acid, and forms body protein on its own and also functions as precursors of materials having various physiological activities. Metabolic pathway of tryptophan in the body is mainly classified into three pathways: serotonin pathway, kynurenine pathway and metabolic pathway by intestinal microbes. In the serotonin pathway, serotonin is biologically synthesized from tryptophan by a tryptophan metabolism enzyme, tryptophan hydroxylase (TPH). In the kynurenine pathway, tryptophan is degraded to kynurenine by indoleamine-pyrrole 2,3-dioxygenase (IDO) and tryptophan 2,3-dioxygenase (TDO). Then, the kynurenine is metabolized to anthranilic acid, nicotinamide and nicotinic acid. In the metabolic pathway by intestinal microbes, tryptophan is degraded to indole by intestinal microbes, transferred to the liver, metabolized to indole sulfate (3-indoxyl sulfate) in the liver, and then excreted through the kidney.

REFERENCES OF THE RELATED ART

Non-Patent Document

1. Zhu W, Stevens A P, Dettmer K, Gottfried E, Noyes S, Kreutz M, Holler E, Canelas A B, Kema I, Oefner P J. Quantitative profiling of tryptophan metabolites in serum, urine, and cell culture supernatants by liquid chromatography-tandem mass spectrometry. Anal Bioanal Chem. 2011 December; 401(10):3249-61.
2. Surjana D, Halliday G M, Damian D L. Role of nicotinamide in DNA damage, mutagenesis, and DNA repair. J Nucleic Acids. 2010; 2010: 157591.
3. Sucher R, Kurz K, Weiss G, Margreiter R, Fuchs D, Brandacher G. IDO-Mediated Tryptophan Degradation in the Pathogenesis of Malignant Tumor Disease. Int J Tryptophan Res. 2010; 3:113-20.

SUMMARY

In one aspect, the present disclosure is directed to providing information, which may be used as basic data for stomach cancer diagnosis by using change of tryptophan metabolism and change of the metabolism rate in human blood.

In another aspect, the present disclosure is directed to providing information, which may be used as basic data for stomach cancer diagnosis by using concentration change of tryptophan, anthranilic acid, serotonin, kynurenine, indole sulfate, nicotinic acid and nicotinamide in human blood.

In still another aspect, the present disclosure is directed to providing a method for analyzing blood by using tryptophan metabolism rate in human blood.

In a further aspect, the present disclosure is directed to providing a method for analyzing blood by using concentration change of tryptophan, anthranilic acid, serotonin, indole sulfate, nicotinic acid and nicotinamide in human blood.

In one aspect, there is provided a method for diagnosing stomach cancer, comprising: measuring concentrations of tryptophan, anthranilic acid, serotonin, kynurenine, indole sulfate, nicotinic acid and nicotinamide in blood collected from an evaluation subject; and diagnosing to have stomach cancer possibility in the case that blood concentration of at least one selected from the group consisting of tryptophan, anthranilic acid, serotonin, kynurenine and indole sulfate is lower than that of blood concentration of a normal person, or in the case that blood concentration of at least one selected from the group consisting of nicotinic acid and nicotinamide is higher than that of blood concentration of a normal person.

In another aspect, there is provided a method for diagnosing stomach cancer, which is to diagnose to have stomach cancer possibility in at least one case selected from the group consisting of: decreasing of blood concentration ratio of anthranilic acid/tryptophan, decreasing of blood concentration ratio of serotonin/tryptophan, increasing of blood concentration ratio of kynurenine/tryptophan, increasing of blood concentration ratio of nicotinic acid/tryptophan and increasing of blood concentration ratio of nicotinamide/tryptophan, compared to a normal person.

In still another aspect, there is provided a method for diagnosing stomach cancer, which is to diagnose to have stomach cancer possibility in at least one case selected from the group consisting of: concentration ratio of anthranilic acid/tryptophan is 0.0005 to 0.003, concentration ratio of serotonin/tryptophan is 0.003 to 0.006, concentration ratio of kynurenine/tryptophan is 0.01 to 0.04, concentration ratio of nicotinic acid/tryptophan is 0.005 to 0.02, and concentration ratio of nicotinamide/tryptophan is 0.05 to 0.08.

In one aspect, there is provided a method for analyzing blood, comprising:

measuring concentrations of tryptophan, anthranilic acid, serotonin, kynurenine, indole sulfate, nicotinic acid and nicotinamide in blood collected from an evaluation subject; and checking whether blood concentration of at least one selected from the group consisting of tryptophan, anthranilic acid, serotonin, kynurenine and indole sulfate is lower than that of blood concentration of a normal person, or blood concentration of at least one selected from the group consisting of nicotinic acid and nicotinamide is higher than that of blood concentration of a normal person or not.

In another aspect, there is provided a method for analyzing blood, which includes checking whether concentration ratio change corresponds to at least one case selected from the group consisting of: decreasing of blood concentration ratio of anthranilic acid/tryptophan, decreasing of blood concentration ratio of serotonin/tryptophan, increasing of blood concentration ratio of kynurenine/tryptophan, increasing of blood concentration ratio of nicotinic acid/tryptophan and increasing of blood concentration ratio of nicotinamide/tryptophan, compared to a normal person, or not.

In still another aspect, there is provided a method for analyzing blood, which includes checking whether concentration ratio corresponds to at least one case selected from the group consisting of: concentration ratio of anthranilic acid/tryptophan is 0.0005 to 0.003, concentration ratio of serotonin/ tryptophan is 0.003 to 0.006, concentration ratio of kynurenine/tryptophan is 0.01 to 0.04, concentration ratio of nicotinic acid/tryptophan is 0.005 to 0.02, and concentration ratio of nicotinamide/tryptophan is 0.05 to 0.08, or not.

In one aspect, whether stomach cancer occurs or not may be easily predicted only through a blood test by using concentration change of tryptophan and its metabolites in blood, or ratio change of tryptophan and its metabolites. Further, whether stomach cancer occurs or not may be diagnosed early and more accurately.

BRIEF DESCRIPTION OF THE DRAWINGS

FIG. 1a shows the results of analyzing tryptophan and all metabolites thereof, and FIG. 1b shows the results of analyzing all metabolites of tryptophan.

DETAILED DESCRIPTION

Figure 1A:
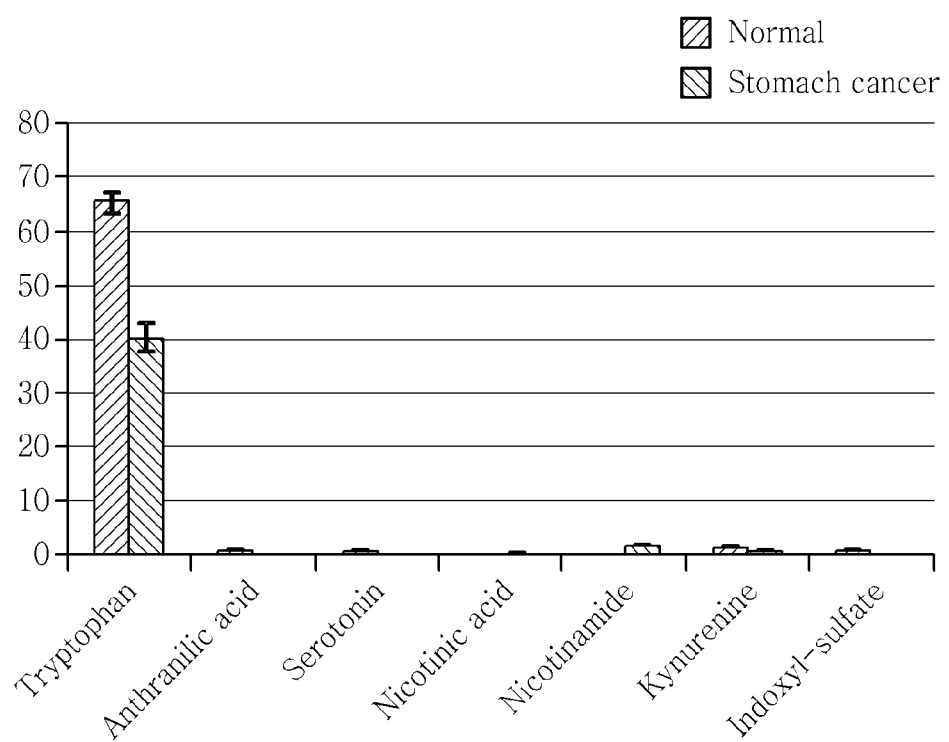
FIGS. 1a and 1b show blood concentrations of tryptophan and metabolites thereof.

Exemplary embodiments now will be described more fully hereinafter with reference to the accompanying drawings, in which exemplary embodiments are shown.

The term "normal person" used herein refers to a mentally and physically healthy mammal including human in one aspect, and it refers to a person who does not have cancer in another aspect.

The term "evaluation subject" used herein refers to a mammal including human in one aspect.

Tryptophan as an essential amino acid and some metabolites thereof are related to cancer. Further, metabolic pathway of kynurenine is activated in various cancer cells including stomach cancer cells, and kynurenine and nicotinamide among the metabolites play a certain role in carcinogenic pathway. Accordingly, after searching metabolic pathway of tryptophan in blood of stomach cancer patients and observing its change feature, many informations, which may judge whether stomach cancer occurs or not, or basic information, which may be used as one of basic data for judging, may be obtained.

In one aspect, the present disclosure provides a method for diagnosing stomach cancer or a method for analyzing blood, which includes measuring concentration by quantitatively analyzing tryptophan and its metabolites in blood of a stomach cancer patient and a normal person, calculating ratio of each metabolite to tryptophan therefrom, comparing metabolism rates of the normal person and the stomach cancer patient, and then using the difference for diagnosing stomach cancer or for analyzing blood. Further, the present disclosure provides a method for diagnosing stomach cancer or a method for analyzing blood, which includes quantitatively analyzing tryptophan and its metabolites contained in blood of a stomach cancer patient and a normal person, and using blood concentration change of tryptophan and its metabolites in blood for diagnosing stomach cancer or for analyzing blood.

As a result of measuring concentrations of tryptophan and its metabolites, i.e., serotonin, kynurenine, anthranilic acid, nicotinamide, nicotinic acid and indole sulfate (3-indoxyl sulfate), in a stomach cancer patient group, blood concentrations of nicotinamide and nicotinic acid are significantly increased, compared to blood concentrations in a normal person, but blood concentrations of tryptophan, serotonin, kynurenine, anthranilic acid and indole sulfate are significantly decreased, compared to blood concentrations in a normal person. Further, in order to check metabolism rate of tryptophan in the body, blood concentration ratio of each metabolite to tryptophan blood concentration are calculated. As a result, blood concentration ratios of "serotonin/tryptophan" and "anthranilic acid/tryptophan" in the stomach cancer patient group are more significantly decreased than those in the normal control group, but blood concentration ratios of "kynurenine/tryptophan", "nicotinamide/tryptophan" and "nicotinic acid/tryptophan" are significantly increased.

In one aspect, when the concentration ratio of each metabolite to tryptophan corresponds to at least one case selected from the group consisting of: concentration ratio of anthranilic acid/tryptophan is 0.0005 to 0.003, concentration ratio of serotonin/tryptophan is 0.003 to 0.006, concentration ratio of kynurenine/tryptophan is 0.01 to 0.04, concentration ratio of nicotinic acid/tryptophan is 0.005 to 0.02, and concentration ratio of nicotinamide/tryptophan is 0.05 to 0.08, it may be one of basic information, which may be judged to have stomach cancer possibility.

The examples (and experiments) will now be described. The following examples (and experiments) are for illustrative purposes only and not intended to limit the scope of the present disclosure.

Example 1

Test Subject and Preparation of Standard Solution for Material Subjected to Analysis 1-1: Patient Subjected to Test and Information Thereof Stomach cancer patients and normal persons are collected at Seoul St. Mary's Hospital, Seoul, Republic of Korea. A stomach cancer patient group includes 66 adult stomach cancer patients having stomach cancer of stage 1 to stage 4, and a normal control group includes 39 healthy adults.

1-2: Collection of Blood Sample and Pretreatment Thereof

Venous blood is obtained from test participants, collected in a sterilized plastic test tube, wherein EDTA as an anticoagulant is treated on the surface thereof, and immediately centrifuged. All samples are stored at about −70° C. until used.

As described in reference of related art (Zhu W, et al. Quantitative profiling of tryptophan metabolites in serum, urine, and cell culture supernatants by liquid chromatography-tandem mass spectrometry. *Anal Bioanal Chem.* 2011 December; 401(10):3249-61), a deproteinizing method using methanol is used. To briefly explain, a certain volume of 1% formic acid aqueous solution and internal standard solution (10 μM tryptophan-$d_3$ and 50 μM kynurenic acid-$d_5$) are added to a blood sample melted at room temperature, and ice-cold methanol of 4 times of the above volume is added thereto. And, the resulting solution is completely stirred for several min and centrifuged. A certain amount of supernatant is collected, dried under nitrogen gas, and then dissolved again in a certain volume of 0.1% formic acid aqueous solution for LC-MS/MS analysis.

1-3: Preparation of Standard Solution for Analyzing Tryptophan and its Metabolites As a material subjected to analysis, tryptophan, serotonin, kynurenine, anthranilic acid, nicotinamide, nicotinic acid, indole sulfate and the like are used, and as an internal standard, tryptophan-$d_3$ and kynurenic acid-$d_5$ are used. A standard solution of each material is prepared by dissolving the material again in 0.1% formic acid aqueous solution to make 1 μM, and stored at about −80° C. Right before used for analysis, the standard solution is serially diluted with 0.1% formic acid aqueous solution up to a certain concentration, and then used for analysis.

Example 2

Liquid Chromatography-Mass Spectrometry (LC-MS/MS) Analysis

Analysis of total 7 materials including tryptophan is conducted by using liquid chromatography-Tandem Mass Spectrometry (LC-MS/MS). The materials are analyzed in multiple reaction monitoring (MRM) mode while interconverting to positive mode and negative mode of electrospray ionization (ESI). As a LC column, Atlantis T3 (2.1×150 mm, 3 μm) is used, and column temperature and auto-sampler temperature are set to 35° C. and 4° C., respectively. As a mobile phase, 0.1% formic acid-containing 5% methanol (mobile phase A) and 0.1% formic acid-containing 95% methanol (mobile phase B) are used, and the analysis is conducted at gradient condition.

Example 3

Figure 1B:
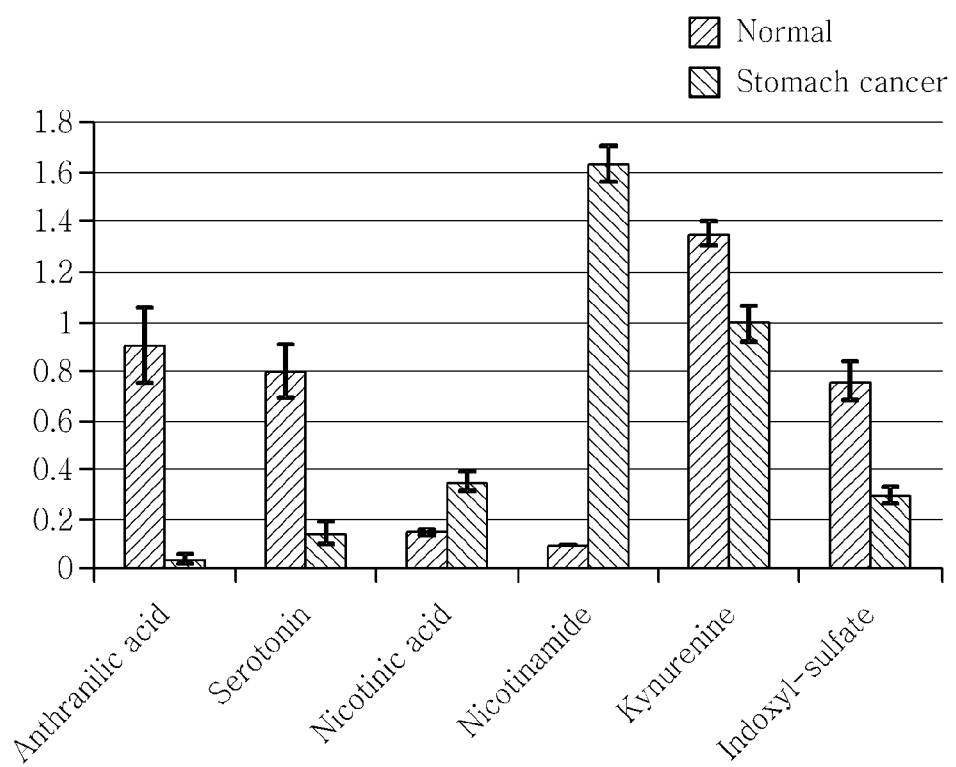

Quantitative Analysis of Tryptophan and its Metabolites in Blood of Stomach Cancer Patient Group and Normal Control Group Blood concentrations of tryptophan and its metabolites are calculated by applying mass analysis data obtained from all samples to calibration curve. Significant differences of when comparing blood concentrations of tryptophan and its metabolites in the normal control group and the stomach cancer patient group are verified by conducting Student t-test. The results are shown in Table 1 and FIGS. 1a and 1b.

TABLE 1

| Material Name | Blood Concentration of Normal Control Group | | Blood Concentration of Stomach Cancer Patient Group | | P-value |
|---|---|---|---|---|---|
| | Mean | Standard Deviation | Mean | Standard Deviation | |
| Tryptophan | 65.72821 | 1.53674 | 40.29705 | 2.54039 | <0.01 |
| Anthranilic acid | 0.900513 | 0.1519605 | 0.041268 | 0.01693 | <0.01 |
| Serotonin | 0.800128 | 0.106607 | 0.147875 | 0.044741 | <0.01 |
| Nicotinic Acid | 0.149667 | 0.012755 | 0.352834 | 0.035486 | <0.01 |
| Nicotinamide | 0.095062 | 0.001432 | 1.63071 | 0.740712 | <0.01 |
| Kynurenine | 1.351282 | 0.482658 | 0.992892 | 0.739419 | 0.09 |
| 3-Indoxyl Sulfate | 7.585641 | 0.78212 | 3.026382 | 0.343759 | <0.01 |

As shown in the above Table 1, blood concentrations of tryptophan, anthranilic acid, serotonin, kynurenine and indole sulfate are significantly reduced in the stomach cancer patient group, compared to the normal control group, but blood concentrations of nicotinamide and nicotinic acid are significantly increased.

Example 4

Confirmation of Metabolic Pathway Ratio of Tryptophan

Figure 2:
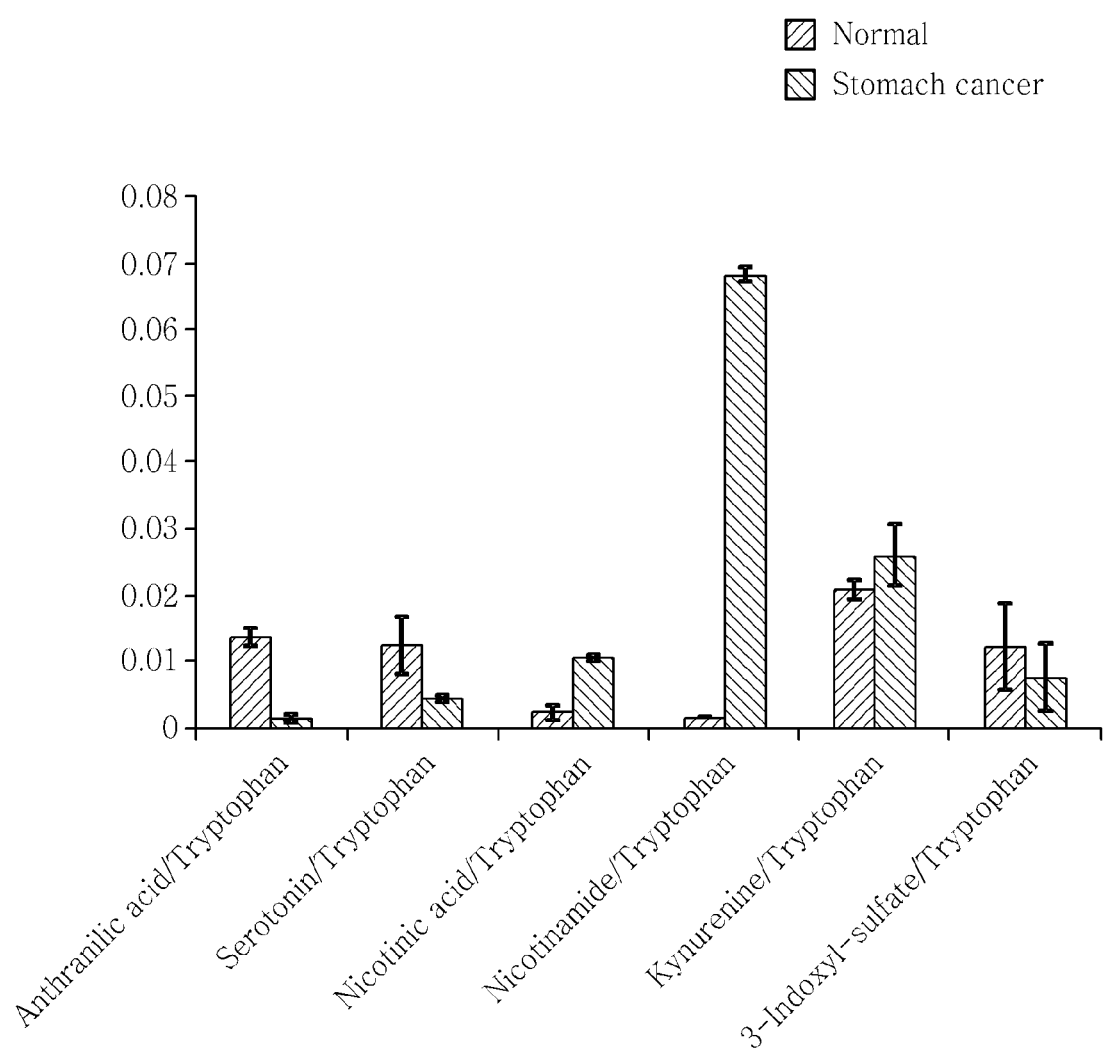
FIG. 2 shows ratio of blood concentrations of tryptophan and metabolites thereof.

In order to confirm ratio of tryptophan metabolic pathway in the normal control group and the stomach cancer patient group, blood concentration ratio of each metabolite to blood concentration of tryptophan is calculated, and differences between the two groups are compared. Significant differences are verified by conducting Student t-test, and the results are shown in Table 2. Further, blood concentration ratios of tryptophan and its metabolites are shown in FIG. 2.

TABLE 2

| Ratio | Blood Concentration Ratio of Normal Control Group | | Blood Concentration Ratio of Stomach Cancer Patient Group | | P-value |
|---|---|---|---|---|---|
| | Mean | Standard Deviation | Mean | Standard Deviation | |
| Anthranilic acid/Tryptophan | 0.013576 | 0.001249 | 0.001372 | 0.000649 | 0.001249 |
| Serotonin/Tryptophan | 0.012401 | 0.004304 | 0.004381 | 0.000466 | 0.004304 |
| Nicotinic acid/Tryptophan | 0.002289 | 0.001141 | 0.01047 | 0.000562 | 0.001141 |
| Nicotinamide/Tryptophan | 0.001465 | 0.000155 | 0.068215 | 0.001107 | 0.000155 |
| Kynurenine/Tryptophan | 0.020768 | 0.001466 | 0.025921 | 0.004704 | 0.001466 |
| 3-Indoxyl Sulfate/Tryptophan | 0.01209 | 0.0065383 | 0.007602 | 0.0050593 | 0.065383 |

As shown in the above Table 2, ratios of "serotonin/tryptophan" and "anthranilic acid/tryptophan" in blood of the stomach cancer patient group are significantly reduced, compared to the normal control group, but ratios of "kynurenine/tryptophan", "nicotinamide/tryptophan" and "nicotinic acid/tryptophan" are significantly increased. Through this, it is confirmed that metabolism rate to the serotonin pathway among tryptophan metabolic pathways is reduced in the stomach cancer patient group, but metabolism rate to the kynurenine pathway is increased, and metabolism rate to the intestinal microbe pathway is not affected.

In one aspect, if concentration ratio corresponds to at least one case selected from: concentration ratio of anthranilic acid/tryptophan is 0.0001 to 0.010, concentration ratio of serotonin/tryptophan is 0.001 to 0.010, concentration ratio of kynurenine/tryptophan is 0.005 to 0.10, concentration ratio of nicotinic acid/tryptophan is 0.001 to 0.10 and concentration ratio of nicotinamide/tryptophan is 0.01 to 0.15, it may be diagnosed to have stomach cancer possibility.

In another aspect, concentration ratio of anthranilic acid/tryptophan may be 0.0001 to 0.010, 0.0002 to 0.007 or 0.0003 to 0.005. In one aspect, concentration ratio of serotonin/tryptophan may be 0.001 to 0.010, 0.001 to 0.008 or 0.002 to 0.007. In one aspect, concentration ratio of kynurenine/tryptophan may be 0.005 to 0.10, 0.007 to 0.08 or 0.008 to 0.06. In one aspect, concentration ratio of nicotinic acid/tryptophan may be 0.001 to 0.10, 0.003 to 0.08 or 0.003 to 0.05. In one aspect, concentration ratio of nicotinamide/tryptophan may be 0.01 to 0.15, 0.02 to 0.12 or 0.03 to 0.10.

In still another aspect, if concentration ratio corresponds to at least one case selected from: concentration ratio of anthranilic acid/tryptophan is 0.0005 to 0.003, concentration ratio of serotonin/tryptophan is 0.003 to 0.006, concentration ratio of kynurenine/tryptophan is 0.01 to 0.04, concentration ratio of nicotinic acid/tryptophan is 0.005 to 0.02 and concentration ratio of nicotinamide/tryptophan is 0.05 to 0.08, it may be diagnosed to have stomach cancer possibility.

Figure 3:
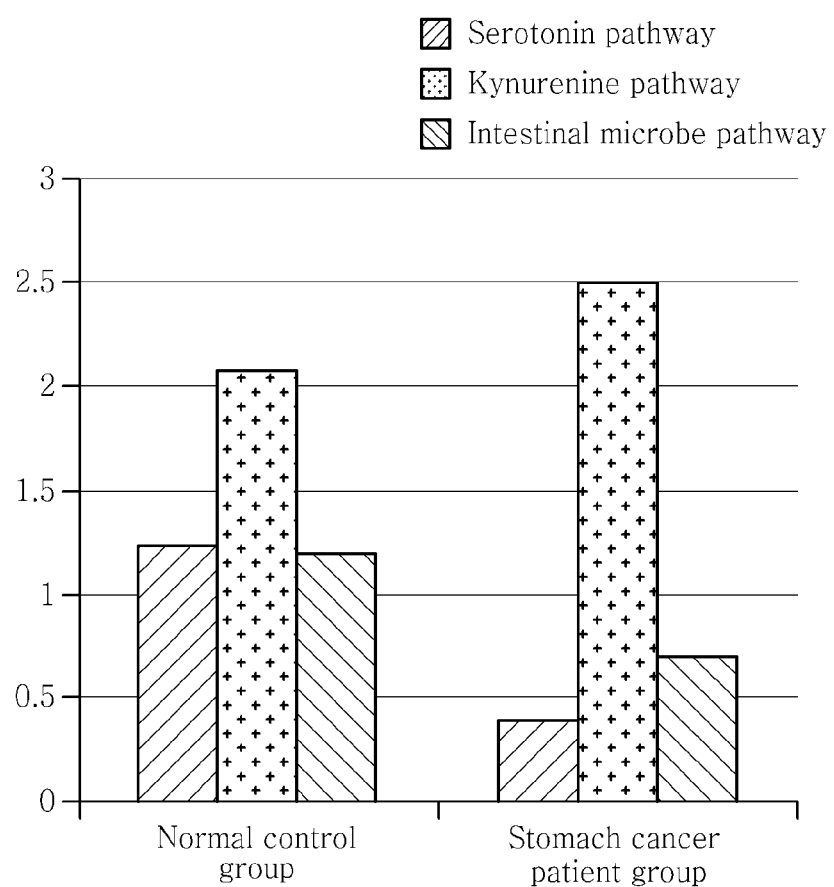
FIG. 3 shows ratio of tryptophan metabolic pathway in a normal control group and a stomach cancer patient group.

Each metabolic pathway ratio in the normal control group and the stomach cancer patient group is calculated by comparing "serotonin/tryptophan", "kynurenine/tryptophan" and "indole sulfate/tryptophan", and the results are shown in Table 3 and FIG. 3.

TABLE 3

|  | Serotonin Pathway | Kynurenine Pathway | Intestinal Microbe Pathway |
|---|---|---|---|
| Normal Control Group | 1.24 | 2.08 | 1.2 |
| Stomach Cancer Patient Group | 0.4 | 2.5 | 0.7 |

While the exemplary embodiments have been shown and described, it will be understood by those skilled in the art that various changes in form and details may be made thereto without departing from the spirit and scope of the present disclosure as defined by the appended claims.

What is claimed is:

1. A method for diagnosing stomach cancer comprising:
collecting a blood sample from an evaluation subject and centrifuging the blood sample;
deproteinizing the centrifuged blood sample by adding methanol to the centrifuged blood sample;
analyzing tryptophan and its metabolites in the centrifuged and deproteinized blood sample of the evaluation subject using mass spectrometry, wherein the analyzing tryptophan and its metabolites comprises:
measuring concentrations of tryptophan, anthranilic acid, serotonin, kynurenine, indole sulfate, nicotinic acid and nicotinamide in the centrifuged and deproteinized blood sample collected from the evaluation subject; and
determining that the evaluation subject has stomach cancer possibility in at least one case selected from the group consisting of: concentration ratio of anthranilic acid/tryptophan of 0.0005 to 0.003, concentration ratio of serotonin/tryptophan of 0.003 to 0.006, concentration ratio of kynurenine/tryptophan of 0.01 to 0.04, concentration ratio of nicotinic acid/tryptophan of 0.005 to 0.02, and concentration ratio of nicotinamide/tryptophan of 0.05 to 0.08.

2. The method for diagnosing stomach cancer according to claim 1, wherein the measuring concentration comprises preparing a standard solution using formic acid aqueous solution.

3. The method for diagnosing stomach cancer according to claim 1, wherein the measuring concentration comprises analyzing mass using liquid chromatography-mass spectrometry.

4. The method for diagnosing stomach cancer according to claim 3, wherein the using liquid chromatography-mass spectrometry further comprises analyzing in multiple reaction monitoring (MRM) mode while interconverting to positive mode and negative mode of electrospray ionization (ESI).

* * * * *